United States Patent

Coffindaffer et al.

[11] Patent Number: 6,007,802
[45] Date of Patent: Dec. 28, 1999

[54] CONDITIONING SHAMPOO COMPOSITION

[75] Inventors: Timothy Woodrow Coffindaffer, Loveland; Everett Junior Inman, Cincinnati; Susan Marie Guskey, Montgomery; Elizabeth Murphy Schrader, Loveland; Robert Lee Wells; John Thomas Baravetto, both of Cincinnati, all of Ohio

[73] Assignee: The Procter & Gamble Co., Cincinnati, Ohio

[21] Appl. No.: 08/624,869

[22] Filed: Mar. 27, 1996

[51] Int. Cl.$^6$ .............. A61K 7/06; A61K 7/08; A61K 7/48
[52] U.S. Cl. .................. 424/70.19; 424/70.1; 424/70.11; 424/70.12; 424/70.21
[58] Field of Search ............. 424/70.11, 70.12, 424/70.19, 70.21, 70.1

[56] References Cited

U.S. PATENT DOCUMENTS

| | | | |
|---|---|---|---|
| 2,826,551 | 3/1958 | Green | 252/89 |
| 3,149,178 | 9/1964 | Hamilton | 260/683.9 |
| 3,382,291 | 5/1968 | Brennan | 260/683.15 |
| 3,725,498 | 4/1973 | Brennan | 260/683.15 B |
| 3,964,500 | 6/1976 | Drakoff | 132/7 |
| 4,167,486 | 9/1979 | Rowe | 252/56 R |
| 4,175,046 | 11/1979 | Coant et al. | 252/56 S |
| 4,304,678 | 12/1981 | Schick et al. | 252/56 R |
| 4,364,837 | 12/1982 | Pader | 252/173 |
| 4,524,007 | 6/1985 | Chibnik | 252/56 R |
| 4,555,353 | 11/1985 | Horodysky et al. | 252/49.6 |
| 4,587,026 | 5/1986 | Horodysky | 252/47.5 |
| 4,657,690 | 4/1987 | Grollier et al. | 252/90 |
| 4,664,835 | 5/1987 | Grollier et al. | 252/90 |
| 4,741,855 | 5/1988 | Grote et al. | 252/142 |
| 4,806,345 | 2/1989 | Bhattacharyya | 424/70 |
| 4,834,893 | 5/1989 | Doner et al. | 252/32.7 E |
| 4,967,029 | 10/1990 | Wu | 585/12 |
| 5,011,681 | 4/1991 | Ciotti et al. | 424/81 |
| 5,019,282 | 5/1991 | Farng et al. | 252/32.7 E |
| 5,085,857 | 2/1992 | Reid et al. | 424/70 |
| 5,105,038 | 4/1992 | Chen et al. | 585/10 |
| 5,221,530 | 6/1993 | Janchitraponvej et al. | 424/70 |
| 5,338,470 | 8/1994 | Heibert et al. | 252/51.5 |
| 5,417,965 | 5/1995 | Janchitraponvej | 424/70 |

FOREIGN PATENT DOCUMENTS

| | | | |
|---|---|---|---|
| 9462606 | 9/1994 | Australia | A61K 7/48 |
| 0 413 416 A2 | 2/1991 | European Pat. Off. | A61K 7/06 |
| 0 413 417 B2 | 2/1991 | European Pat. Off. | A61K 7/08 |
| 0521665A1 | 1/1993 | European Pat. Off. | A61K 7/06 |
| 54-129135 | 10/1979 | Japan | A61K 7/06 |
| 56-72095 | 6/1981 | Japan | C11D 3/37 |
| 1-168612 | 12/1987 | Japan | A61K 7/50 |
| 849433 | 9/1960 | United Kingdom . | |
| WO 93/08787 | 5/1993 | WIPO | A61K 7/06 |
| WO 95/02388 | 1/1995 | WIPO . | |

*Primary Examiner*—Thurman K. Page
*Assistant Examiner*—Brian K. Seidlock
*Attorney, Agent, or Firm*—William J. Winter; Darryl C. Little

[57] ABSTRACT

Disclosed are aqueous hair conditioning shampoo compositions comprising a specific surfactant component comprising an ethoxylated alkyl sulfate surfactant having from about 1 to about 8 moles of ethoxylation and an amphoteric surfactant in a shampoo with insoluble, dispersed conditioning agent, select esters and a select soluble cellulosic cationic organic polymer hair conditioning agent.

17 Claims, No Drawings

CONDITIONING SHAMPOO COMPOSITION

FIELD OF THE INVENTION

This invention relates to conditioning shampoo compositions containing a specific surfactant component comprising an ethoxylated alkyl sulfate surfactant having from about 1 to about 8 moles of ethoxylation and an amphoteric surfactant in a shampoo with insoluble, dispersed, nonionic conditioning agent, select synthetic esters and a select soluble cellulosic cationic organic polymer hair conditioning agent. The compositions provide improved hair conditioning performance, including improved wet hair feel.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. Shampooing can also result in the hair becoming dry or "frizzy", and a loss of luster, due to removal of natural oils or other hair moisturizing materials. After shampooing, the hair can also suffer from a loss of "softness" perceived by the user upon drying. The hair can also suffer from increased levels of static upon drying after shampooing. This can interfere with combing and can result in fly-away hair. A variety of approaches have been developed to alleviate the after-shampoo problems. These range from the inclusion of hair conditioning aids in shampoos to post-shampoo application of hair conditioners, i.e., hair rinses. Hair rinses are generally liquid in nature and must be applied in a separate step following the shampooing, left on the hair for a length of time, and rinsed with fresh water. This, of course, is time consuming and is not as convenient as shampoos containing both cleaning and hair conditioning ingredients.

While a wide variety of shampoos have been disclosed which contain conditioning aids, they have not been totally satisfactory for a variety of reasons; Cationic conditioning agents are highly desirable for use in hair conditioning due to their abilities to control static, improve wet detangling, and provide a silky wet hair feel to the user. One problem which has been encountered in shampoos relates to compatibility problems between good cleaning anionic surfactants and the many conventional cationic agents which historically have been used as conditioning agents. Efforts have been made to minimize adverse interaction through the use of alternate surfactants and improved cationic conditioning agents. Cationic surfactants which provide good overall conditioning in hair rinse products, in general, tend to complex with anionic cleaning surfactants and provide poor conditioning in a shampoo context. In particular, the use of soluble cationic surfactants that form soluble ionic complexes do not deposit well on the hair. Soluble cationic surfactants that form insoluble ionic complexes deposit on the hair but do not provide good hair conditioning benefits, and tend to cause the hair to have a dirty, coated feel. The use of insoluble cationic surfactants, e.g., tricetyl methyl ammonium chloride, can provide excellent anti-static benefits but do not otherwise provide good overall conditioning. Many cationic polymers tend to build up on the hair to result in an undesirable, "unclean" coated feel. Cationic polymers therefore, conventionally, are preferably used at limited levels to minimize this problem. This, however, can limit the overall conditioning benefits that are obtained. Additionally, cationic conditioning agents commonly do not provide optimal overall conditioning benefits, particularly in the area of "softness", especially when delivered as an ingredient in a shampoo composition.

Materials which can provide increased softness are nonionic silicones. Silicones in shampoo compositions have been disclosed in a number of different publications. Such publications include U.S. Pat. No. 2,826,551, Geen, issued Mar. 11, 1958; U.S. Pat. No. 3,964,500, Drakoff, issued Jun. 22, 1976; U.S. Pat. No. 4,364,837, Pader, issued Dec. 21, 1982; and British Patent 849,433, Woolston, issued Sep. 28, 1960. While these patents disclose silicone containing compositions, they also did not provide a totally satisfactory product in that it was difficult to maintain the silicone well dispersed and suspended in the product. Recently, stable, insoluble silicone-containing hair conditioning shampoo compositions have been described in U.S. Pat. No. 4,741,855, Grote and Russell, issued May 3, 1988 and U.S. Pat. No. 4,788,066, Bolich and Williams, issued Nov. 29, 1988. These shampoo compositions can deliver excellent overall conditioning benefits to the hair while maintaining excellent cleaning performance, even with the use of anionic detersive surfactants, for a wide variety of hair types.

More recently, improved conditioning shampoos were provided in U.S. Ser. No. 07/622,699, Robert L. Wells, filed Dec. 5, 1990, now abandoned, and its continuation application Ser. No. 07/778,765, filed Oct. 21, 1991, now abandoned wherein shampoos containing anionic surfactant, dispersed, insoluble silicone, and certain relatively low ionic strength cationic polymers (greater than about 0.4 meq./gm) were disclosed. These compositions provide excellent hair cleaning conditioning to a wide variety of hair types, especially including improved conditioning to hair damaged by color treatments, bleaching, permanents, etc.

Japanese Patent Application, Laid Open No. 56-72095, Jun. 16, 1981, Hirota et al. (Kao Soap Corp.) also discloses shampoo containing cationic polymer and silicone conditioning agents. Still other patent publications relating to shampoos with cationic agents and silicone include EPO Application Publication 0 413 417, published Feb. 20, 1991, Hartnett et al.

Another approach to providing hair conditioning benefits to shampoo compositions has been to use materials which are oily to the touch. These materials provide improved luster and shine to the hair. Oily materials have also been combined with cationic materials in the shampoo formulations. Japanese Patent Application Showa 53-35902, laid open Oct. 6, 1979 (Showa 54-129135), N. Uchino (Lion Yushi Co.), discloses hair treatment compositions containing cationic polymer, fatty acid salt, and at least 10% of an oily component for use before or after shampooing. Suitable oily components are hydrocarbons, higher alcohols, fatty acid esters, glycerides, and fatty acids. Japanese Patent Application 62 [1987]-327266, filed Dec, 25, 1987, published Jul. 4, 1989, laid open No. HEI 1 [1987]-168612, Horie et al., discloses detergent compositions containing cationic surfactant and/or cationic polymer, anionic surfactant, and specific esters of the formula RCOOR' wherein R and R' are straight or branched chain alkyls.

In spite of these attempts to provide optimal combinations of cleaning ability and hair conditioning, it remains desirable to provide further improved hair conditioning shampoo compositions. For instance, it remains desirable to improve overall conditioning, and especially shine and luster, wet and dry combing, and dry hair feel, of hair treated with shampoo containing silicone and cationic material. For shampoos containing oily materials in combination with cationic materials, it remains desirable to improve overall conditioning, especially wet combing and detangling, dry combing, and dry hair feel. However merely increasing the level of one or both conditioning ingredients can result in adverse effects such as greasy hair feel and loss of fullness. It is desirable to improve conditioning without suffering from these drawbacks.

One attempt to do this is disclosed in EPO Patent Publication No. 0 413 416, published Feb. 20, 1991, Robbins et al., which discloses shampoo containing aminosilicone, anionic surfactant, cationic surfactant, and a hydrocarbon component. These types of formulations would normally be expected to result in either excessive buildup of aminosilicone on the hair, and consequently greasy hair feel and loss of fullness, or a relatively limited degree of improvement due to intentional use of very low levels of aminosilicone to avoid such adverse effects. The cationic surfactants would have limited ability to condition the hair due to interaction with the anionic surfactant.

EPO Patent Application Publication No. 0 413 417, published Feb. 20, 1991, discloses shampoo containing anionic surfactant, and conditioning agents such as insoluble silicone (preferably aminosilicone), cationic surfactant, polyethylenes, paraffins, microcrystalline waxes, $C_{18}$–$C_{36}$ fatty acids or triglycerides, high fatty alcohol esters of high fatty acids, and beeswax. Another patent document which discloses shampoo compositions and a variety of conditioning agents is U.S. Pat. No. 3,964,500, Drakoff, issued Jun. 22, 1976. This patent relates to shampoo containing silicone conditioner and a hair bodying agent selected from certain wood rosins, shellac, sucrose acetate isobutyrate, and cationic amino cellulose.

A recent approach to providing hair conditioning benefits to shampoo is described in U.S. Pat. No. 5,085,857 (Reid et al.). The composition disclosed combines a surfactant system (selected from anionic, nonionic, or amphoteric, or mixtures thereof), cationic guar derived polymer, and nonvolatile silicone having particle size less than 2 microns. Without being limited by theory, Applicants have found that by utilizing a select cationic cellulose derived polymer in place of the cationic guar derived polymer in a specific surfactant system, which optimizes the conditioning coacervate formed, the present invention results in significantly improved conditioning performance.

In spite of all these approaches and attempts to provide optimum combinations of shampoos and hair conditioners, it remains desirable to provide still improved conditioning shampoos. It has now been found that improved overall conditioning can be achieved by combining a specific surfactant component comprising an ethoxylated alkyl sulfate surfactant having from about 1 to about 8 moles of ethoxylation and an amphoteric surfactant in a shampoo with insoluble, dispersed, nonionic conditioning agent, select synthetic esters and a soluble cellulosic cationic organic polymer hair conditioning agent. These compositions can provide improved conditioning while reducing the level of undesirable side effects that can result from increasing the level of conditioning agent in prior known conditioning systems. As discussed previously, a conditioning agent system containing too much silicone can result in silicone build up on the hair over repeated usages and to loss of fullness of the hair. Too much oil results in an oily feel and a loss of fullness of the hair. Too much cationic conditioning agent results in a coated, dirty feel of the hair. Now it has been found that the components of the present invention can provide improved overall conditioning while minimizing the adverse effects of conditioning agent build-up that otherwise can be incurred upon increasing the levels of individual components in prior known conditioning systems. It has now been found that by adding select synthetic esters improves conditioning benefits.

It is an object of this invention to provide shampoo compositions, which can provide excellent cleaning performance and improved levels of conditioning while minimizing any adverse side effects associated with build-up due to the use of excess conditioning agent.

It is also an object of this invention to provide a method for cleaning and conditioning the hair which can provide excellent cleaning in combination with improved conditioning, while minimizing adverse side effects associated with excess build-up of conditioning agent on the hair.

These objects will become apparent from the description which follows, as may other objects become apparent upon a reading of said description.

SUMMARY OF THE INVENTION

The present invention is directed to hair conditioning shampoo compositions comprising:

a) from about 5.0% to about 50 % of a surfactant component comprising: i) an ethoxylated alkyl sulfate surfactant having from about 1 to about 8 moles of ethoxylation; and ii) an amphoteric surfactant;

b) from about 0.01% to about 3.0% of a cationic cellulosic polymer having a molecular weight of from about 400,000 to about 1,500,000 and charge density of from about 0.6 to about 3 meq/g.;

c) from about 0.005% to about 5% of a water insoluble non-volatile conditioning agent having an average particle size below about 4 microns;

(d) from about 0.01% to about 1.0% by weight of water insoluble, synthetic esters having a viscosity of from about 1 to about 300 centipoise, and which conforms to either of the following formulas

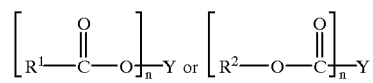

wherein $R^1$ is an alkyl, alkenyl, hydroxyalkyl or hydroxyalkenyl group, having from 7 to 9 carbon atoms; n is a positive integer having a value of from 2 to 4; $R^2$ is an alkyl, alkenyl, hydroxyalkyl or hydroxyalkenyl group, having from 8 to 10 carbon atoms; and Y is an alkyl, alkenyl, or a hydroxy or carboxy substituted allyl or alkenyl, having from 2 to 20 carbon atoms; and e) an aqueous carrier wherein said composition comprises less than about 5% of ethoxylated alkyl sulfate surfactant having less than 1 mole of ethoxylation and wherein the synthetic ester content represents from about 2.5% to about 100% by weight of the total liquid fatty ester content of the composition. The shampoo compositions provide improved conditioning performance, including improved wet hair feel.

DETAILED DESCRIPTION OF THE INVENTION

The shampoo compositions of the present invention can comprise, consist of, or consist essentially of the essential elements and limitations of the invention described herein, as well any of the additional or optional ingredients, components, or limitations described herein.

All percentages, parts and ratios are based upon the total weight of the shampoo compositions of the present invention, unless otherwise specified. All such weights as they pertain to listed ingredients are based on the active level and, therefore, do not include carriers or by-products that may be included in commercially available materials, unless otherwise specified.

As used herein, the term "soluble" refers to any material that is sufficiently soluble in water to form a substantially clear solution to the naked eye at a concentration of 0.1% by weight of the material in water at 25° C. Conversely, the term "insoluble" refers to all other materials that are therefore not sufficently soluble in water to form a substantially clear solution to the naked eye at a concentration of 0.1% by weight of the other material in water at 25° C.

As used herein, the term "low viscosity" refers to a viscosity of from about 1 to about 300 centipoise, preferably from about 1 to about 150 centipoise, more preferably from about 2 to about 50 centipoise. All viscosity values herein are measured at a temperature of 40° C. by the ASTM D-445 method.

As used herein, the term "liquid" refers to any visibly (by the naked eye) flowable fluid under ambient conditions (about 1 atmosphere of pressure at about 25° C.)

The shampoo compositions of the present invention, including the essential and optional components thereof, are described in detail hereinafter.

Surfactant Component

Alkyl Ether Surfactant

The shampoo compositions of the present invention comprise from about 5.0% to about 50% of a detersive surfactant component comprising: i) an ethoxylated alkyl sulfate surfactant having from about 1 to about 8 moles of ethoxylation; and ii) an amphoteric surfactant component to provide cleaning performance to the composition and wherein said the resulting composition comprises less than about 5%, preferably less than about 3% and most preferably less than about 2% of alkyl sulfate ethoxylated surfactant having less than 1 mole of ethoxylation The detersive surfactant component can optionally comprises additional detersive surfactants. Such surfactants should be physically and chemically compatible with the essential components described herein, or should not otherwise unduly impair product stability, aesthetics or performance.

Concentration of the surfactant component in the shampoo composition ranges from about 5% to about 50%, preferably from about 8% to about 30%, more preferably from about 10% to about 25%, even more preferably from about 12% to about 20%, by weight of the composition.

The alkyl ether sulfates have the formula: $RO(C_2H_4O)_xSO_3M$, wherein R is alkyl or alkenyl of from about 8 to about 24 carbon atoms, x is 1 to 8, and M is a cation such as ammonium, alkanolamines, such as triethanolamine, monovalent metals, such as sodium and potassium, and polyvalent metal cations, such as magnesium, and calcium. The cation M, of the anionic detersive surfactant should be chosen such that the detersive surfactant component is water soluble. Solubility will depend upon the particular anionic detersive surfactants and cations chosen.

Preferably, R has from about 8 to about 18 carbon atoms, more preferably from about 10 to about 16 carbon atoms, most preferably from about 12 to about 14 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm kernal or tallow, or can be synthetic. Lauryl alcohol and straight chain alcohols derived from coconut oil or palm kernal are preferred herein. Such alcohols are reacted with between about 1 and about 10, and especially about 3, molar proportions of ethylene oxide and the resulting mixture of molecular species having, for example, an average of 3 moles of ethylene oxide per mole of alcohol, is sulfated and neutralized.

Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Amphoteric Surfactant

Suitable amphoteric surfactant components for use in the shampoo composition herein include those which are known for use in shampoo compositions or other personal care cleansing composition, and which contain a group that is anionic at the pH of the shampoo composition. Concentration of such surfactant components in the shampoo composition preferably ranges from about 0.5% to about 20%, preferably from about 1% to about 10%, more preferably from about 2% to about 5% by weight of the composition. Examples of amphoteric surfactants suitable for use in the shampoo compostion herein are described in U.S. Pat. No. 5,104,646 (Bolich Jr. et al.), U.S. Pat. No. 5,106,609 (Bolich Jr. et al.), which descriptions are incorporated herein by reference. Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378.

Other amphoterics, sometimes classified as zwitterionics, such as betaines can also useful in the present invention. Such zwitterionics are considered as amphoterics in the present invention where the zwitterionic has an attached group that is anionic at the pH of the composition. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH(CH$_2$)$_3$ radical is attached to the nitrogen atom of the betaine are also useful in this invention. Most preferred for use herein is cocoamidopropyl betaine.

The shampoo compositions of the present invention may further comprise additional detersive surfactants for use in combination with the anionic detersive surfactant component described hereinbefore. Suitable optional surfactants include nonionic surfactants, cationic surfactants, and combinations thereof. Any such surfactant known in the art for use in hair or personal care products may be used, provided that the optional additional surfactant is also chemically and physically compatible with the essential components of the shampoo composition, or does not otherwise unduly impair product performance, aesthetics or stability. Concentration of the optional additional surfactants in the shampoo composition may vary with the cleaning or lather performance desired, the optional surfactant selected, the desired product concentration, the presence of other components in the composition, and other factors well known in the art.

Preferred for use are optional anionic detersive surfactants which can be used in addition to the alkyl ether sulfates are the water-soluble salts of organic, sulfuric acid reaction products of the general formula [R$_1$—SO$_3$—M] where R$_1$ is selected from the group consisting of a straight or branched chain, saturated aliphatic hydrocarbon radical having from about 8 to about 24, preferably about 10 to about 18, carbon atoms; and M is a cation, as previously described, subject to the same limitations regarding polyvalent metal cations as previously discussed. Examples of such detersive surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., SO$_3$, H$_2$SO$_4$, obtained according to known sulfonation methods, including bleaching and hydrolysis. Preferred are alkali metal and ammonium sulfonated C$_{10-18}$ n-paraffins.

Still other suitable anionic detersive surfactants are the reaction products of fatty acids esterified with isethionic acid and neutralized with sodium hydroxide where, for example, the fatty acids are derived from coconut oil or palm kernal oil; sodium or potassium salts of fatty acid amides of methyl tauride in which the fatty acids, for example, are derived from coconut oil or palm kernal oil. Other similar anionic surfactants are described in U.S. Pat. No. 2,486,921; U.S. Pat. No. 2,486,922; and U.S. Pat. No. 2,396,278, which descriptions are incorporated herein by reference.

Other anionic detersive surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; dioctyl esters of sodium sulfosuccinic acid.

Other suitable anionic detersive surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid SO$_2$, chlorinated hydrocarbons, etc., when used in the liquid form, or by air, nitrogen, gaseous SO$_2$, etc., when used in the gaseous form.

The alpha-olefins from which the olefin sulfonates are derived are mono-olefins having about 10 to about 24 carbon atoms, preferably about 12 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880, which description is incorporated herein by reference.

Another class of anionic detersive surfactants suitable for use in the shampoo compositions are the beta-alkyloxy alkane sulfonates. These compounds have the following formula:

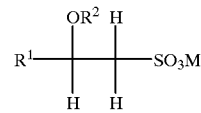

where R$^1$ is a straight chain alkyl group having from about 6 to about 20 carbon atoms, R$^2$ is a lower alkyl group having from about 1 (preferred) to about 3 carbon atoms, and M is a water-soluble cation as hereinbefore described.

Preferred additional anionic detersive surfactants for use in the shampoo compositions include ammonium lauryl sulfate, ammonium laureth sulfate, triethylamine lauryl sulfate, tri-ethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Cationic Hair Conditioning Polymer

Cationic cellulosic derivative polymer materials suitable for use herein include those of the formula:

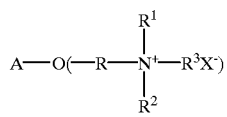

wherein:

A is a cellulose anhydroglucose residual,

R is an alkylene, oxyalkylene, polyoxyalkylene, or hydroxyalkylene group, or combination thereof, R$^1$, R$^2$, and R$^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

The cationic cellulosic polymer has a molecular weight ranging from about 400,000 to about 1,500,000, preferably from about 500,000 to about 1,500,000 and most preferably from about 800,000 to about 1,200,000 and a charge density of from about 0.6 to about 3 meq./gr, preferably from about 0.7 to about 2.0 meq/gr. and most preferably from about 0.9 to about 1.5 meq/gr. Cationic cellulose is available from Amerchol Corp. (Edison, N.J., USA) in their Polymer JR and LR series of polymers, as salts of hydroxyethyl cellulose reacted with trimethyl ammonium substituted epoxide, referred to in the industry (CTFA) as Polyquaternium 10.

The water soluble cationic described herein are either soluble in the shampoo composition, or preferably are soluble in a complex coacervate phase in the shampoo composition formed by the cationic polymer and the anionic surfactant described hereinbefore. Complex coacervates of the cationic polymer can also be formed with other optional anionic components of the shampoo composition.

Coacervate formation is dependent upon a variety of criteria such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", *Cosmetics & Toiletries*, Vol. 106, April 1991, pp 49–54, C. J. van Oss, "Coacervation, Complex-Coacervation and Flocculation", *J. Dispersion Science and Technology*, Vol. 9 (5,6), 1988–89, pp 561–573, and D. J. Burgess, "Practical Analysis of Complex Coacervate Systems", *J. of Colloid and Interface Science*, Vol. 140, No. 1, November 1990, pp 227–238, which descriptions are incorporated herein by reference.

It is believed to be particularly advantageous for the cationic polymer to be present in the shampoo composition in a coacervate phase, or to form a coacervate phase upon application or rinsing of the shampoo to or from the hair. Complex coacervates are believed to more readily deposit on the hair. Thus, in general, it is preferred that the cationic polymer exist in the shampoo composition as a coacervate phase or form a coacervate phase upon dilution. If not already a coacervate in the shampoo composition, the cationic polymer will preferably exist in a complex coacervate form in the shampoo upon dilution with water.

Techniques for analysis of formation of complex coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the shampoo composition.

Insoluble Hair Conditioning Agent

The shampoo compositions of the present invention further comprises an insoluble hair conditioning agent at concentrations effective to provide hair conditioning benefits. Such concentrations generally range from about 0.005% to about 5%, preferably from about 0.05% to about 4%, more preferably from about 0.1% to about 3.5%, most preferably from about 0.2% to about 3%, by weight of the shampoo compositions. The insoluble hair conditioning particles useful in the present invention have a particle size range below about 4 microns, preferably below about 1 micron, most preferably below about 0.5 microns. Useful conditioning agents include silicone and petrolatum.

Silicone Hair Conditioning Agent

Most preferred for use herein are non-volatile silicone conditioning agents. Typically it will be intermixed in the shampoo composition so as to be in the form of a separate, discontinuous phase of dispersed, insoluble particles, also referred to as droplets. These droplets may be suspended with a suspending agent described hereinafter. The silicone hair conditioning agent phase will comprise a silicone fluid hair conditioning agent such as a silicone fluid and can also comprise other ingredients, such as a silicone resin to enhance silicone fluid deposition efficiency or enhance glossiness of the hair (especially when high refractive index (e.g. above about 1.46) silicone conditioning agents are used (e.g. highly phenylated silicones).

As used herein, "nonvolatile" refers to silicone material with little or no significant vapor pressure under ambient conditions, as is understood by those in the art. Boiling point under one atmosphere (atm) will preferably be at least about 250° C., more preferably at least about 275° C., most preferably at least about 300° C. Vapor pressure is preferably about 0.2 mm HG at 25° C. or less, preferably about 0.1 mm HG at 25° C. or less.

The silicone hair conditioning agent phase may comprise volatile silicone, nonvolatile silicone, or mixtures thereof. Typically, if volatile silicones are present, it will be incidental to their use as a solvent or carrier for commercially available forms of nonvolatile silicone materials ingredients, such as silicone gums and resins.

The silicone hair conditioning agents for use in the shampoo compositions preferably have a viscosity of from about 20 to about 2,000,000 centistokes, more preferably from about 1,000 to about 1,800,000 centistokes, even more preferably from about 10,000 to about 1,500,000 centistokes, most preferably from about 30,000 to about 1,000,000 centistokes, at 25° C. The viscosity can be measured by means of a glass capillary viscometer as set forth in Dow Corning Corporate Test Method CTM0004, Jul. 20, 1970.

Optional silicone fluid for use in the shampoo compositions includes silicone oil which are flowable silicone materials with a viscosity of less than 1,000,000 centistokes, preferably between about 5 and 1,000,000 centistokes, more preferably between about 10 and about 600,000 centistokes, more preferably between about 10 and about 500,000 centistokes, most preferably between 10 and 300,000 centistokes at 25° C. Suitable silicone oils include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used.

Optional Silicone oils for use in the composition include polyalkyl or polyaryl siloxanes which conform to following formula:

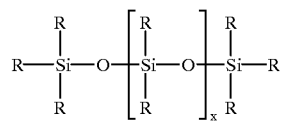

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions, and are capable of being deposited on and, of conditioning, the hair.

The two R groups on the silicon atom of each monomeric silicone unit may represent the same group or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Suitable alkylamino substituted silicones include those conforming to the following formula:

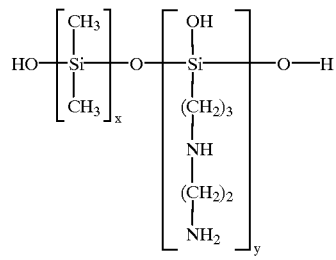

wherein x and y are integers. This polymer is also known as "amodimethicone".

Suitable cationic silicone fluids include those conforming to the formula described hereinabove, wherein $(R_1)_a G_{3-a}$—Si—$(—OSiG_2)_n$—$(—OSiG_b(R_1)_{2-b})_m$—O—$SiG_{3a}(R_1)_a$ in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical of formula $CqH_{2q}L$ in which q is an integer from 2 to 8 and L is chosen from the groups —$N(R_2)CH_2$—$CH_2$—$N(R_2)_2$
—$N(R_2)_2$
—$N(R_2)_3 A^-$
—$N(R_2)CH_2$—$CH_2$—$NR_2H_2 A^-$ in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred cationic silicone corresponding to the previous formula is the polymer known as "trimethylsilylamodimethicone", which conforms to the following formula:

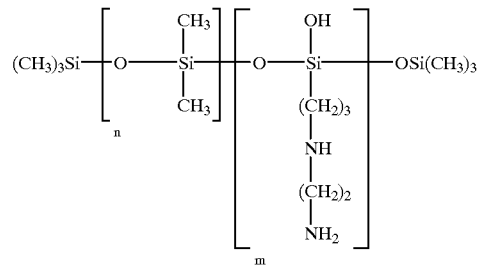

Other silicone cationic polymers which can be used in the shampoo compositions are those which conform to the following formula:

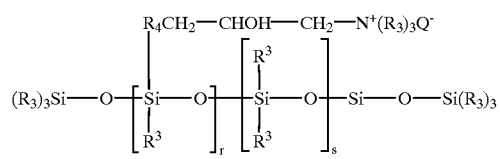

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–C8, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

Other suitable silicone fluids for use in the silicone conditioning agents are insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones* New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

The silicone hair conditioning agent can also comprise a mixture of polydimethylsiloxane gum (viscosity greater than about 1,000,000 centistokes) and polydimethylsiloxane oil (viscosity from about 10 to about 100,000 centistokes), wherein the ratio of gum to fluid is from about 30:70 to about 70:30, preferably from about 40:60 to about 60:40.

Another category of nonvolatile, insoluble silicone fluid conditioning agents are high refractive index silicones, having a refractive index of at least about 1.46, preferably at least about 1.48, more preferably at least about 1.52, most preferably at least about 1.55. Although not intended to necessarily be limiting, the refractive index of the polysiloxane fluid will generally be less than about 1.70, typically less than about 1.60. Polysiloxane "fluid" includes oils as well as gums.

The high refractive index polysiloxane fluid suitable for purposes hereof includes those conforming to the formula described hereinabove, as well as cyclic polysiloxanes such as those conforming to the following formula:

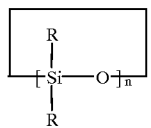

wherein R is as defined above, n is from about 3 to about 7, preferably from 3 to 5.

The high refractive index polysiloxane fluids contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/cm$^2$, typically at least about 27 dynes/cm$^2$. Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —R$^1$ NHR$^2$NH2 where each R$^1$ and R$^2$ independently is a $C_1$–$C_3$ alkyl, alkenyl, and/or alkoxy. High refractive index polysiloxanes are available from Dow Corning Corporation (Midland, Mich., U.S.A.) Huls America (Piscataway, N.J., U.S.A.), and General Electric Silicones (Waterford, N.Y., U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture can provide improved shine enhancement of the hair.

Also, the spreading agent will preferably reduce the surface tension by at least about 2 dynes/cm$^2$, preferably at least about 3 dynes/cm$^2$, even more preferably at least about 4 dynes/cm$^2$, most preferably at least about 5 dynes/cm$^2$.

The surface tension of the mixture of the polysiloxane fluid and the spreading agent, at the proportions present in the final product, is preferably 30 dynes/cm$^2$ or less, more preferably about 28 dynes/cm$^2$ or less most preferably about 25 dynes/cm$^2$ or less. Typically the surface tension will be in the range of from about 15 to about 30, more typically from about 18 to about 28, and most generally from about 20 to about 25 dynes/cm$^2$.

The weight ratio of the highly arylated polysiloxane fluid to the spreading agent will, in general, be between about 1000:1 and about 1:1, preferably between about 100:1 and about 2:1, more preferably between about 50:1 and about 2:1, most preferably from about 25:1 to about 2:1. When fluorinated surfactants are used, particularly high polysiloxane: spreading agent ratios may be effective due to the efficiency of these surfactants. Thus it is contemplated that ratios significantly above 1000:1 may be used.

References disclosing examples of some suitable silicone fluids for use in the shampoo compositions include U.S. Pat. Nos. 2,826,551, 3,964,500, 4,364,837, British Patent 849, 433, and *Silicon Compounds*. Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

The shampoo composition of the present invention may further comprise a suspending agent for the insoluble conditioning agent. Such suspending agents are well known in the shampoo and conditioning art. Examples of some suitable suspending agents are described in U.S. Pat. Nos. 4,741,855, 4,788,006, 4,704,272, 2,798,053, which descriptions are incorporated herein by reference. Suitable suspending agents for use in combination with the insoluble conditioning agent include acyl derivatives, long chain amine oxides, xantham gum, and carboxyvinyl polymers. Other suitable suspending agents include primary amines having a fatty alkyl moiety having at least about 16 carbon atoms, secondary amines having two fatty alkyl moieties each having at least about 12 carbon atoms, di(hydrogenated tallow)phthalic acid amide, and crosslinked maleic anhydride-methyl vinyl ether copolymer.

Other suitable suspending agents for use in combination with the insoluble conditioning agent include those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydorxethylcellulose), guar gum, polyvinyl alcohol, polyvinyl pyrrolidone, hydroxypropyl guar gum, starch and starch derivatives, and other thickeners, viscosity modifiers, gelling agents, and so forth.

Synthetic Esters

The shampoo composition of the present invention comprise select synthetic esters at concentrations ranging from about 0.01% to about 1.0%, preferably from about 0.05% to about 0.5%, more preferably from about 0.08% to about 0.3%, by weight of the shampoo composition. These select esters provide improved wet hair feel when used in combination with the essential components of the shampoo composition herein, and in particular when used in combination with the cationic hair conditioning polymer described hereinbefore.

The synthetic esters for use in the shampoo composition are water insoluble and have a viscosity of from about 1 to about 300 centipoise, preferably from about 1 to about 150 centipoise, more preferably from about 2 to about 50 centipoise. The synthetic esters conform to either of the following Formulas I or II

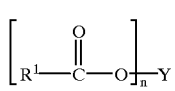

-continued

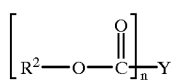
(II)

wherein $R^1$ is an alkyl, alkenyl, hydroxyalkyl or hydroxyalkenyl group, having from 7 to 9 carbon atoms, preferably a saturated alkyl group, more preferably a saturated, linear, alkyl group; n is a positive integer having a value of from 2 to 4, preferably 3; $R^2$ is an alkyl, alkenyl, hydroxyalkyl or hydroxyalkenyl group, having from 8 to 10 carbon atoms, preferably a saturated alkyl group, more preferably a saturated, linear, alkyl group; and Y is an alkyl, alkenyl, hydroxy or carboxy substituted alkyl or alkenyl, having from about 2 to about 20 carbon atoms, preferably from about 3 to about 14 carbon atoms.

It has been found that this select group of synthetic esters provides improved wet hair feel when used in combination with the essential components of the shampoo composition herein, and in particular when used in combination with the cationic hair conditioning polymer of the shampoo composition. These synthetic esters improve wet hair feel by reducing the slimy or excessively conditioned feel of wet hair that has been conditioned by a cationic hair conditioning polymer. By application of the shampoo composition herein, cleansed and conditioned hair remains detangled and silky during and after the shampooing process, but the excessively conditioned or slimy wet hair feel undesirably associated with good conditioning performance is minimized or eliminated.

Specific non limiting examples of suitable synthetic esters for use in the shampoo composition include P-43 (C8–C10 triester of trimethylolpropane), MCP-684 (tetraester of 3,3 diethanol-1,5 pentadiol), MCP 121 (C8–10 diester of adipic acid), all of which are available from Mobil Chemical Company, Edison, N.J., U.S.A.

In addition to the synthetic esters described hereinbefore, the shampoo compositions may further comprise other organic, hair conditioning oils, including fatty esters other than the select synthetic esters. When such optional conditioning oils are added to the shampoo composition, the select synthetic ester component must still represent at least about 2.5% of the total liquid fatty ester content. The synthetic ester preferably represents from about 2.5% to about 100%, preferably from about 10% to about 100%, more preferably from about 50% to about 100%, even more preferably from about 90% to about 100%, and most preferably about 100%, of the total liquid fatty ester content of the shampoo composition. As used herein, the term "total fatty ester content" refers to the total weight percent of liquid monoesters, diesters, triesters and tetraesters in the shampoo composition.

Water

The shampoo compositions of the present invention comprise from about 20% to about 94%, preferably from about 50% to about 94%, more preferably from about 60% to about 85%, by weight of water.

Other Optional Components

The shampoo compositions of the present invention may further comprise one or more optional components known for use in shampoo or conditioning compositions, provided that the optional components are physically and chemically compatible with the essential component described herein, or do not otherwise unduly impair product stability, aesthetics or performance. Concentrations of such optional components typically range from about 0.001% to about 10% by weight of the shampoo compositions.

Optional components include anti static agents, dyes, organic solvents or diluents, pearlescent aids, foam boosters, additional surfactants or cosurfactants (nonionic, cationic, zwitterionic), pediculocides, pH adjusting agents, perfumes, preservatives, proteins, skin active agents, suspending agents, styling polymers, sunscreens, thickeners, vitamins, and viscosity adjusting agents. This list of optional components is not meant to be exclusive, and other optional components can be used.

Method of Manufacture

The shampoo compositions of the present invention can be prepared by using various formulation and mixing techniques or methods known in the art for preparing surfactant or conditioning compositions, or other similar compositions.

Method of Use

The shampoo compositions of the present invention are used in a conventional manner for cleansing and conditioning hair or skin. An effective amount of the composition for cleansing and conditioning the hair or skin is applied to the hair or skin, that has preferably been wetted with water, and then rinsed off. Such effective amounts generally range from about 1 g to about 50 g, preferably from about 1 g to about 20 g. Application to the hair typically includes working the composition through the hair such that most or all of the hair is contacted with the composition.

This method for cleansing and conditioning the hair comprises the steps of: a) wetting the hair with water, b) applying an effective amount of the shampoo composition to the hair, and c) rinsing the shampoo composition from the hair using water. These steps can be repeated as many times as desired to achieve the desired cleansing and conditioning benefit.

EXAMPLES

The shampoo compositions illustrated in Examples I–XV illustrate specific embodiments of the shampoo compositions of the present invention, but are not intended to be limiting thereof. Other modifications can be undertaken by the skilled artisan without departing from the spirit and scope of this invention. These exemplified embodiments of the shampoo compositions of the present invention provide cleansing of hair and improved hair conditioning performance.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

| Component | Example Number | | | | |
| --- | --- | --- | --- | --- | --- |
| | I | II | III | IV | V |
| Ammonium Laureth-3 Sulfate | 14.00 | 14.00 | 14.00 | 14.00 | 14.00 |
| Cocamidopropylbetaine | 2.70 | 2.70 | 2.70 | 2.70 | 2.70 |
| Polyquaternium-10 (3) | 0.15 | 0.15 | 0.15 | 0.30 | 0.30 |
| C8/C10 diester of adipic acid (4) | 0.30 | 0.15 | 0.10 | 0.30 | 0.15 |

-continued

| Component | | | | | |
|---|---|---|---|---|---|
| Cocamide MEA | 0.80 | 0.80 | 0.80 | 0.80 | 0.80 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| Ethylene Glycol Distearate | 1.50 | 1.50 | 1.50 | 1.50 | 1.50 |
| Dimethicone (1) | 1.00 | 1.00 | 1.00 | 3.00 | 1.00 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

| | Example Number | | | | |
|---|---|---|---|---|---|
| Component | VI | VII | VIII | IX | X |
| Ammonium Laureth-3 Sulfate | 14.00 | 11.75 | 12.50 | 14.85 | 12.50 |
| Cocamidopropylbetaine | 2.70 | 2.25 | 4.20 | 1.85 | 4.20 |
| Polyquaternium-10 (3) | 0.30 | 0.15 | 0.15 | 0.30 | 0.30 |
| Trimethylolpropane caprylate caprate (5) | 0.30 | 0.30 | 0.15 | 0.60 | 0.30 |
| Cocamide MEA | 0.80 | 0.80 | 0.80 | 0.80 | 0 |
| Cetyl Alcohol | 0 | 0.42 | 0.42 | 0.42 | 0.42 |
| Stearyl Alcohol | 0 | 0.18 | 0.18 | 0.18 | 0.18 |
| Ethylene Glycol Distearate | 1.50 | 1.50 | 1.50 | 1.50 | 1.50 |
| Dimethicone (l) | 1.00 | 3.00 | 1.00 | 1.00 | 1.00 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

| | Example Number | | | | |
|---|---|---|---|---|---|
| Component | XI | XII | XIII | XIV | XV |
| Ammonium Laureth-3 Sulfate | 14.00 | 14.00 | 14.00 | 10.00 | 10.00 |
| Cocamidopropylbetaine | 2.70 | 2.70 | 2.70 | 2.00 | 2.00 |
| Polyquaternium-10 (3) | 0.15 | 0.15 | 0.30 | 0.10 | 0.10 |
| C8/C10 diester of adipic acid (4) | 0.15 | 0.30 | 0.10 | 0.10 | 0.15 |
| Cocamide MEA | 0.80 | 0.80 | 0 | 0.80 | 0.60 |
| Cetyl Alcohol | 0 | 0.42 | 0 | 0.42 | 0 |
| Stearyl Alcohol | 0 | 0.18 | 0 | 0.18 | 0 |
| Ethylene Glycol Distearate | 0 | 0 | 0 | 1.50 | 1.50 |
| Carbopol 981 (2) | 0.50 | 0.50 | 0.50 | 0 | 0 |
| Dimethicone (1) | 1.00 | 1.00 | 1.00 | 1.00 | 0.50 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

(1) Dimethicone is an emulsion of 60,000 csk polydimethyl siloxane with particle size of approximnately 300 nm available from Dow Corning (DC 1664).
(2) Carbopol 981 is a crosslinked polyacrylate available from B. F. Goodrich.
(3) Polyquaternium-10 is UCare Polymer JR30M available from Amerchol.
(4) C8/C10 diester of adipic acid is MCP 121 available from Mobil Chemical.
(5) Trimethylolpropane caprylate caprate is P43 available from Mobil Chemical.

What is claimed is:

1. An aqueous shampoo composition comprising:

a) from about 5.0% to about 50% of a surfactant component comprising:
 i) an ethoxylated alkyl sulfate surfactant having from about 1 to about 8 moles of ethoxylation; and
 ii) an amphoteric surfactant;

b) from about 0.01% to about 3.0% of a cationic cellulosic polymer having a molecular weight of from about 400,000 to about 1,500,000 and charge density of from about 0.6 to about 3 meq/gram;

c) from about 0.005% to about 5% of a water insoluble non-volatile silicone conditioning agent having an average particle size below about 4 microns;

d) from about 0.01% to about 1.0% by weight of a water insoluble, synthetic ester having a viscosity of from about 1 to about 300 centipoise, and which conforms to either of the following formulas

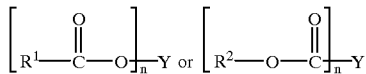

wherein $R^1$ is an alkyl, alkenyl, hydroxyalkyl or hydroxyalkenyl group, having from 7 to 9 carbon atoms; n is a positive integer having a value of from 2 to 4; $R^2$ is an alkyl, alkenyl, hydroxyalkyl or hydroxyalkenyl group, having from 8 to 10 carbon atoms; and Y is an alkyl, alkenyl, or a hydroxy or carboxy substituted alkyl or alkenyl, having from 2 to 20 carbon atoms; and e) an aqueous carrier wherein said composition comprises less than about 5% of ethoxylated alkyl sulfate surfactant having less than 1 mole of ethoxylation and wherein the synthetic ester content represents from about 2.5% to about 100% by weight of the total liquid fatty ester content of the composition.

2. An aqueous shampoo composition according to claim 1 which comprises from about 8.0% to about 30% of said surfactant component and wherein said composition comprises less than about 3% of ethoxylated surfactant having less than 1 mole of ethoxylation and wherein said amphoteric surfactant is cocoamidopropyl betaine and wherein said non-volatile conditioning agent is a silicone.

3. A shampoo composition as in claim 2, wherein said component (d) has viscosity of from about 1 to about 150 centipoise.

4. A shampoo composition as in claim 3, wherein in said component (d) $R^1$ and $R^2$ are independently a saturated alkyl group.

5. A shampoo composition as in claim 4, wherein said synthetic esters are selected from the group consisting of C8–C10 triester of trimethylolpropane, C8–C10 tetraester of 3,3 diethanol-1,5 pentadiol, C8–C10 diester of adipic acid, and mixtures thereof.

6. An aqueous shampoo composition according to claim 2 wherein said nonvolatile silicone conditioning agent is selected from the group consisting of polyarylsiloxanes, polyalkyl siloxanes, polyalkylarylsiloxanes, derivatives thereof, and mixtures thereof.

7. An aqueous shampoo composition according to claim 6 wherein nonvolatile silicone conditioning agent has an average particle size of less than about 1 micron.

8. An aqueous shampoo composition according to claim 7 wherein nonvolatile silicone conditioning agent has an average particle size of less than about 0.5 microns.

9. An aqueous shampoo composition according to claim 8 wherein nonvolatile silicone conditioning agent is polydimethylsiloxane.

10. An aqueous shampoo composition according to claim 9 wherein said cationic polymer hair conditioning agent has a cationic charge density of from about 0.7 meq/gram to about 2.0 meq/gram.

11. An aqueous shampoo composition according to claim 10 wherein said cationic polymer hair conditioning agent has a cationic charge density of from about 0.9 meq/gram to about 1.5 meq./gram.

12. An aqueous shampoo composition according to claim 1 wherein said cationic cellulosic polymer hair conditioning agent is Polyquaternium-10.

13. An aqueous shampoo composition according to claim 2 wherein said amphoteric surfactant is cocoamidopropyl betaine and comprises from about 1% to about 10% of the composition.

14. An aqueous shampoo composition according to claim 13 wherein said amphoteric surfactant is cocoamidopropyl betaine and comprises from about 2% to about 5% of the composition.

15. An aqueous shampoo composition according to claim 1 wherein non-volatile silicone conditioning agent comprises from about 0.05% to about 4% of the composition.

16. An aqueous shampoo composition according to claim 1 wherein non-volatile silicone conditioning agent comprises from about 0.2% to about 3% of the composition.

17. An aqueous shampoo composition according to claim 16 wherein said cationic polymer hair conditioning agent has a molecular weight of from about 800,000 to about 1,200,000.

* * * * *